United States Patent
Magna et al.

(10) Patent No.: US 9,931,622 B2
(45) Date of Patent: Apr. 3, 2018

(54) CATALYTIC COMPOSITION AND PROCESS FOR THE SELECTIVE DIMERIZATION OF ETHYLENE TO 1-BUTENE

(71) Applicant: IFP Energies Nouvelles, Rueil-Malmaison (FR)

(72) Inventors: Lionel Magna, Lyons (FR); Helene Olivier-Bourbigou, Saint Genis-Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/790,841

(22) Filed: Jul. 2, 2015

(65) Prior Publication Data

US 2016/0002124 A1    Jan. 7, 2016

(30) Foreign Application Priority Data

Jul. 4, 2014 (FR) ..................... 14 56471

(51) Int. Cl.
| | |
|---|---|
| *C07C 2/00* | (2006.01) |
| *C07C 2/30* | (2006.01) |
| *B01J 37/00* | (2006.01) |
| *B01J 31/14* | (2006.01) |
| *B01J 31/02* | (2006.01) |
| *B01J 31/12* | (2006.01) |

(52) U.S. Cl.
CPC .......... *B01J 37/00* (2013.01); *B01J 31/0212* (2013.01); *B01J 31/128* (2013.01); *B01J 31/143* (2013.01); *C07C 2/30* (2013.01); *B01J 2231/20* (2013.01); *C07C 2531/12* (2013.01); *C07C 2531/14* (2013.01); *Y02P 20/52* (2015.11)

(58) Field of Classification Search
CPC ..... C07C 2/08; C07C 2/06; C07C 2/02; B01J 31/0212; B01J 31/0214; B01J 31/128; B01J 31/38

See application file for complete search history.

(56) References Cited

U.S. PATENT DOCUMENTS

| | | | | |
|---|---|---|---|---|
| 3,969,429 | A * | 7/1976 | Belov | C07C 2/30 585/512 |
| 4,532,370 | A * | 7/1985 | Le Quan | B01J 31/0212 585/512 |
| 4,721,762 | A * | 1/1988 | Commereuc | C08F 210/16 502/126 |
| 5,024,982 | A * | 6/1991 | Hawley | C08F 10/00 502/104 |
| 5,030,790 | A * | 7/1991 | Sergienko | C07C 2/30 585/512 |
| 6,228,957 | B1 * | 5/2001 | Ford | C08F 10/00 502/103 |
| 2011/0288308 | A1 * | 11/2011 | Grasset | B01J 31/0212 549/210 |
| 2016/0002123 | A1 * | 1/2016 | Magna | C07C 2/30 585/512 |
| 2017/0007994 | A1 * | 1/2017 | Lucciulli | B01J 31/0204 |

FOREIGN PATENT DOCUMENTS

| | | | | |
|---|---|---|---|---|
| EP | 200 654 A1 * | 12/1986 | ............. | C07C 11/08 |
| EP | 0 516 852 A1 * | 12/1992 | ............. | C07C 11/08 |
| EP | 0516852 A1 | 12/1992 | | |
| FR | 2552079 A1 | 3/1985 | | |
| GB | 2 231 583 A * | 11/1990 | ............... | C07C 2/30 |
| JP | 6-157634 A * | 6/1994 | ............. | C08F 4/652 |
| SU | 658119 A1 * | 4/1979 | ............. | C07C 11/02 |

OTHER PUBLICATIONS

EP 0 516 852 A1 (Zhukov et al.) Dec. 9, 1992; machine translation.*
Belov et al. (SU 658119 A1), Apr. 25, 1979; machine translation.*
Search Report and Opinion from corresponding French Patent Application No. 14/56471 dated Mar. 12, 2015.

* cited by examiner

*Primary Examiner* — Rip A Lee
(74) *Attorney, Agent, or Firm* — Millen, White, Zelano & Branigan, P.C.

(57) ABSTRACT

The invention describes a catalytic composition obtained by interaction of an alkyl titanate on the one hand with a preformed mixture of an alkylaluminium and a Lewis base on the other hand. The invention also describes the use of said composition in a process for the selective dimerization of ethylene to 1-butene.

14 Claims, No Drawings

CATALYTIC COMPOSITION AND PROCESS FOR THE SELECTIVE DIMERIZATION OF ETHYLENE TO 1-BUTENE

The present invention relates to a catalytic composition and a process for the selective dimerization of ethylene to 1-butene using said catalytic composition.

PRIOR ART

Among the catalytic systems which are capable of selectively dimerizing ethylene to 1-butene, it is possible to identify in the literature catalytic systems based on vanadium (S. Zhang et al. *Organometallics* 2009, 28, 5925; K. Nomura et al. *Inorg. Chem.* 2013, 52, 2607), iron or cobalt (S. Song et al. *J. Organomet. Chem.*, 2011, 696, 2594; V. Appukuttan et al. *Organometallics* 2011, 30, 2285), tungsten (H. Olivier et al. *J. Mol. Catal. A: Chem.* 1999, 148, 43; R. Tooze et al. Sasol Technology WO2005089940A2, 2005), tantalum (S. McLain et al. *J. Am. Chem. Soc.*, 1978, 100(4), 1315; R. Schrock et al. *Pure & App. Chem.*, 1980, 52, 729), nickel (S. Mukherjee et al. *Organometallics* 2009, 28, 3074; K. Wang et al. *Catal. Commun.* 2009, 10, 1730; H. Liu et al. *Dalton Trans.* 2011, 40, 2614; J. Flapper et al. *Organometallics* 2009, 28, 3272, K. Song et al. *Eur. J. Inorg. Chem.* 2009, 3016) or indeed titanium (A. W. AlSa'doun, *Applied Catalysis A: General*, 1993, 105, 1-40).

Of these systems, those based on titanium are by far the best. In the patent U.S. Pat. No. 2,943,125, K. Ziegler describes a process for the dimerization of ethylene to 1-butene using a catalyst obtained by mixing trialkylaluminium and a titanium or zirconium tetraalcoholate. During the reaction, a certain quantity of high molecular mass polymer (namely polyethylene) is also formed; this has a considerable deleterious effect on the implementation of the process. Several improvements have been proposed in order to reduce the quantity of polyethylene formed, in particular in the patent U.S. Pat. No. 3,686,350, which recommends the use of organic phosphorus compounds jointly with the elements of the catalyst. In the patent U.S. Pat. No. 3,879,485, another improvement consists of using various ethers as solvents for the reaction medium. Although these modifications to the initial catalytic system substantially improve the selectivity of the reaction, they turn out to be of little practical use, in particular in an industrial process in which the 1-butene has to be separated from the solvent leaving only traces of polar compound in the butenes.

From this point of view, the Applicant's patent FR 2 552 079 has demonstrated that using a catalyst obtained by the interaction of a trialkylaluminium on the one hand with a pre-formed mixture of alkyl titanate and an ether type additive in stoichiometric quantities on the other hand appreciably improves the activity and selectivity of such catalysts for the dimerization of ethylene to 1-butene. However, low but measurable quantities of polymer have been detected in the examples of that patent.

The principal disadvantage of catalytic systems based on titanium resulting in the selective formation of 1-butene is the formation of a non-negligible quantity of polymers, namely polyethylene. This polyethylene formation may be the source of rapid deactivation of the catalyst and increased difficulties with operability.

One aim of the invention is to provide a particular catalytic composition which, when used in a process for the selective dimerization of ethylene to 1-butene, results in a reduced or even near-zero production of polyethylene compared with the prior art.

DETAILED DESCRIPTION OF THE INVENTION

The systems based on titanium described above principally use a trialkylaluminium type derivative, in particular triethylaluminium, as the co-catalyst (or activator). This compound is described in the literature as a dimeric species ($Al_2Et_6$) and is characterized, inter alia, by a high reactivity with Lewis base (LB) type compounds. This reaction, which is generally highly exothermic, results in the formation of novel stable aluminium complexes which can very often be purified by vacuum distillation. These complexes are generally monomeric with a LB/Al stoichiometry of 1/1. They are in the form of a white solid or a colourless liquid. Their physico-chemical properties are also very different from those of the starting triethylaluminium. An example that may be cited is the considerable reduction of the Lewis acidity of these complexes compared with the starting triethylaluminium (Dailey et al., *J. Am. Chem. Soc*, 1956, 77, 3977; Y. Takashi, *Bull. Chem. Soc. Jpn*, 1967, 40, 612).

It has now been discovered that a catalytic composition obtained by mixing an alkoxy or aryloxy titanium compound with a preformed mixture of a Lewis base type additive and an aluminium compound in proportions close to stoichiometry has a very high selectivity and activity for the selective dimerization of ethylene to 1-butene and has a reduced or even zero production of polyethylene.

Without wishing to be bound by any particular theory, it might be imagined that using a preformed mixture of a Lewis base type additive and an aluminium compound means that in contact with the titanium compound, the generation of catalytic species responsible for the production of polymer would be limited.

The term "proportions close to stoichiometry or stoichiometric quantity" means that the Lewis base type additives (LB) are used or mixed with the aluminium compound (Al) in a "LB/Al" molar ratio which is strictly more than 0.5, preferably strictly more than 1, preferably in the range from a value strictly more than 0.5 to 20, and more preferably in the range from a value strictly more than 1 to 20. Preferably, the molar ratio "LB/Al" is in the range from a value strictly more than 0.5 to 5, more preferably in the range from a value strictly more than 1 to 5.

In the remainder of the text and above, unless indicated otherwise, the molar ratio between the Lewis base (LB) type additive and the aluminium compound (Al) will be expressed in moles of Lewis base type additive per mole of aluminium (Al). In the same manner, unless indicated otherwise, the molar ratio between the aluminium compound and the titanium alkoxy or aryloxy compound will be expressed in moles of aluminium per mole of titanium.

The term "Lewis base" means any molecular entity or any corresponding chemical species which can supply an electron pair and is thus capable of becoming coordinated with a Lewis acid, thereby producing a Lewis adduct.

The term "preformed mixture" means that the Lewis base type additive and the aluminium compound are brought into contact separately from the other compounds of the catalytic composition prior to them being used in the catalytic composition. Preferably, this contact is made by adding a stoichiometric quantity of Lewis base type additive to the aluminium compound in order to form an adduct.

The alkoxy titanium compounds used in the present invention advantageously have the general formula [Ti(OR)$_4$], in which R is a linear or branched alkyl radical containing 2 to 30 carbon atoms. The radical R may comprise substituents based on a nitrogen, phosphorus, sulphur and oxygen heteroatom.

Non-limiting examples of preferred alkoxy radicals which may be cited include: tetraethoxy, tetraisopropoxy, tetra-n-butoxy and tetra-2-ethyl-hexyloxy.

The aryloxy titanium compounds used in the present invention advantageously have the general formula [Ti(OR')$_4$], in which R' is an aryl radical which may or may not be substituted with alkyl, aryl or aralkyl groups containing 2 to 30 carbon atoms. The radical R' may comprise substituents based on a nitrogen, phosphorus, sulphur and oxygen heteroatom.

Non-limiting examples of preferred aryloxy radicals which may be cited include: phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-tert-butyl-6-phenylphenoxy, 2,4-di-tert-butyl-6-phenylphenoxy, 2,6-diisopropylphenoxy, 2,6-di-tert-butylphenoxy, 4-methyl-2,6-di-tert-butylphenoxy, 2,6-dichloro-4-tert-butylphenoxy and 2,6-dibromo-4-tert-butylphenoxy, the biphenoxy radical, binaphthoxy, and 1,8-naphtalene-dioxy.

The aluminium compound of the invention is advantageously selected from the group formed by hydrocarbylaluminium compounds, tris(hydrocarbyl)aluminium compounds, chlorine-containing or bromine-containing hydrocarbylaluminium compounds and aluminoxanes; preferably, said aluminium compound is advantageously selected from the group formed by hydrocarbylaluminium compounds, tris(hydrocarbyl)aluminium compounds and chlorine-containing or bromine-containing hydrocarbylaluminium compounds.

The tris(hydrocarbyl)aluminium compounds and the chlorine-containing or bromine-containing hydrocarbylaluminium compounds are represented by the general formula AlR"$_m$Y$_{3-m}$ in which R" is a hydrocarbyl radical, preferably alkyl containing 1 to 6 carbon atoms, Y is a chlorine or bromine atom, preferably a chlorine atom, and m is a number from 1 to 3.

Preferably, the aluminium compound is selected from the group formed by dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$). The preferred aluminium compound is triethylaluminium (AlEt$_3$).

The Lewis base type additive of the catalytic composition in accordance with the invention is advantageously selected from compounds of the ether, amine, phosphine, or sulphide type, which may be cyclic or non-cyclic, substituted or not substituted with alkyl, aryl or aralkyl groups containing 2 to 30 carbon atoms.

The ether type compounds are advantageously selected from monoethers and polyethers. Preferred ether type compounds which may be cited by way of non-limiting example include: diethyl ether, diisopropylether, dibutylether, diphenylether, 2-methoxy-2-methylpropane, 2-methoxy-2-methylbutane, dimethoxy-2,2 propane, di(ethyl-2 hexyloxy)-2,2 propane, 2,5-dihydrofuran, tetrahydrofuran, 2-methoxytetrahydrofuran, 2-methyltetrahydrofuran, le 3-methyltetrahydrofuran, 2,3-dihydropyran, tetrahydropyran, 1,3-dioxolane, 1,3-dioxane, 1,4-dioxane, dimethoxyethane, di(2-methoxyethyl)ether and benzofuran, glyme and diglyme, used alone or as a mixture.

The amine type compounds are advantageously selected from monoamines, di-, tri- and poly-amines, imines, diimines, pyridines, bipyridines, imidazoles, pyrroles, pyrazoles. Preferred amine type compounds which may be cited by way of non-limiting example include: trimethylamine, triethylamine, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluromethylpyridine, 2-phenylpyridine, 3-phenylpyridine, 2-benzylpyridine, 3,5-dimethylpyridine, 2,6-di-tert-butylpyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethyl-ethane-1,2-diimine, N,N'-di-t-butyl-ethane-1,2-diimine, N,N'-di-t-butyl-butane-2,3-diimine, N,N'-diphenyl-ethane-1,2-diimine, N,N-bis-(dimethyl-2,6-phenyl)-ethane-1,2-diimine, N,N'-bis-(diisopropyl-2,6-phenyl)-ethane-1,2-diimine, N,N'-diphenyl-butane-2,3-diimine, N,N'-bis-(dimethyl-2,6-phenyl)-butane-2,3-diimine, and N,N'-bis-(diisopropyl-2,6-phenyl)-butane-2,3-diimine.

The phosphine type compounds are advantageously selected from phosphines, polyphosphines, phosphine oxides, phosphites, phosphonites and phosphinites. Preferred phosphine type compounds which may be cited by way of non-limiting example include: tributylphosphine, trisopropylphosphine, tricyclohexylphosphine, triphenylphosphine, tris (o-tolyl)phosphine, bis (diphenylphosphino)ethane, trioctylphosphine oxide, triphenylphosphine oxide and triphenylphosphite.

The sulphide type compounds are advantageously selected from mono-sulphides and polysulphides. Preferred sulphide type compounds which may be cited by way of non-limiting example include: diethylsulphide, dimethyldisulphide, tetrahydrothiophene, 2-methylthiophene, 3-methylthiophene, 2-methoxythiophene, 3-methoxythiophene.

The Lewis base (LB) type additives are used or mixed with the aluminium compound (Al) in a "LB/Al" molar ratio which is strictly more than 0.5, preferably strictly more than 1, preferably in the range from a value strictly more than 0.5 to 20 and more preferably in the range from a value strictly more than 1 to 20. Preferably, the molar ratio "LB/Al" is in the range from a value strictly more than 0.5 to 5, more preferably in the range from a value strictly more than 1 to 5.

In accordance with a preferred preparation embodiment, the preformed mixture of the Lewis base type additive and the aluminium compound is produced by adding a stoichiometric quantity of the Lewis base type additive to the aluminium compound. Preferably, this addition is carried out in a dilute medium using a solvent. In this case, the solvent used is advantageously selected from the group formed by aliphatic and cycloaliphatic hydrocarbons such as hexane, cyclohexane, heptane. This mixture is advantageously produced at a temperature in the range −80° C. to +200° C., preferably in the range −40° C. to +100° C., for example at a temperature close to ambient temperature (15° C. to 30° C.).

The alkoxy or aryloxy titanium compound may be used as a mixture with a hydrocarbon type solvent selected from the group formed by aliphatic and cycloaliphatic hydrocarbons such as hexane, cyclohexane, heptane, butane or isobutane, by an unsaturated hydrocarbon such as a monoolefin or a diolefin containing 4 to 20 carbon atoms, for example, by an aromatic hydrocarbon such as benzene, toluene, ortho-xylene, mesitylene, or ethylbenzene, or by a chlorine-containing hydrocarbon such as chlorobenzene or dichloromethane, or with an ether type solvent such as dimethylether, dibutylether, tetrahydrofuran, 1,4-dioxane, pure or as a mixture. Advantageously, aliphatic hydrocarbons such as cyclohexane or n-heptane are used, as well as ethers such as tetrahydrofuran and 1,4-dioxane. The mixture may be produced under an atmosphere of ethylene or inert gas.

In the case in which the alkoxy or aryloxy titanium compound is used as a mixture with a hydrocarbon type solvent, said mixture is advantageously used in a ratio by volume between the solvent and the titanium compound in the range 100/1 to 1/1 (vol/vol). In the case in which the alkoxy or aryloxy titanium compound is used as a mixture with an ether type solvent, said mixture is advantageously used in a molar ratio between the solvent and the alkoxy or aryloxy titanium compound in the range 20/1 to 1/1 (mol/mol).

Dimerization Reaction

The process of the invention is a process for the selective dimerization of ethylene to 1-butene using the catalytic composition described above.

The ethylene dimerization reaction is advantageously carried out under a total pressure of 0.5 to 20 MPa, preferably 0.5 to 15 MPa, preferably 1 to 10 MPa, and at a temperature of 20° C. to 180° C., preferably 40° C. to 140° C.

The molar ratio between the preformed mixture comprising the aluminium compound and the Lewis base type additive on the one hand and the alkoxy or aryloxy titanium compound of the catalytic composition on the other hand is employed such that the molar ratio between the aluminium compound and the titanium compound is in the range 1/1 to 1000/1 mol/mol, preferably in the range 1/1 to 500/1; more preferably, this ratio is less than 100/1 mol/mol.

The concentration of titanium in the catalytic solution is advantageously in the range $1 \times 10^{-9}$ to 1 mol/L, preferably in the range $1 \times 10^{-6}$ to 0.5 mol/L.

In accordance with a preferred embodiment, the dimerization reaction is carried out in batch mode. Selected quantities of solutions of the titanium compound and the preformed mixture of the Lewis base type additive and the aluminium compound are introduced into a reactor provided with the usual stirring, heating and cooling devices, then it is pressurized using ethylene, advantageously to the desired pressure, and the temperature is advantageously adjusted to the desired value. The dimerization reactor is maintained at a constant pressure by introducing ethylene until the total volume of liquid produced represents, for example, 2 to 50 times the volume of the solution containing the catalytic composition originally introduced. The catalyst is then destroyed using any of the usual means known to the skilled person, then the reaction products and the solvent are withdrawn and separated.

In accordance with another preferred embodiment, the catalytic ethylene dimerization reaction is carried out in continuous mode. In a first variation, on the one hand the titanium compound and on the other hand the preformed mixture of the Lewis base type additive and the aluminium compound are separately injected into a reactor maintained under a constant pressure of ethylene. Said reactor is stirred using conventional mechanical means known to the skilled person or by external recirculation. The temperature and pressure of the ethylene are kept constant at the desired values using conventional means known to the skilled person. The reaction mixture is withdrawn using a liquid level-regulated valve in order to keep it constant. The catalyst is continuously destroyed using any of the usual means known to the skilled person, then the products obtained from the reaction as well as the solvent are separated, for example by distillation. The ethylene which has not been transformed may be recycled to the reactor. The residues of catalyst included in a heavy fraction may be incinerated.

In a second variation, on the one hand the titanium compound and on the other hand the preformed mixture of the Lewis base additive and the aluminium compound are injected into a first reactor/mixer; said mixture is then continuously introduced into a reactor maintained under a constant pressure of ethylene. Said mixture in the first reactor/mixer may be produced under an inert atmosphere or under an atmosphere of ethylene. The reaction mixture is withdrawn using a liquid level-regulated valve in order to keep it constant. The catalyst is continuously destroyed using any usual means known to the skilled person, then the products obtained from the reaction as well as the solvent are separated, for example by distillation. The ethylene which has not been transformed may be recycled to the reactor. The residues of catalyst included in a heavy fraction may be incinerated.

Products Obtained

The process of the invention can be used for the selective production of 1-butene. This compound is of use as co-monomers with ethylene in the manufacture of different grades of polyethylene (HDPE, LLDPE, etc.).

The following examples illustrate the invention without limiting its scope.

EXAMPLES

Example 1

Synthesis of the Adduct "THF.AlEt$_3$"

25 mL of n-heptane in which 0.832 g (7.3 mmol) of AlEt$_3$ had been dissolved was introduced into a Schlenk flask under an inert atmosphere. Next, 0.54 g (7.5 mmol) of THF was added in a controlled manner. The solution was stirred at ambient temperature for approximately 1 h. The n-heptane was then eliminated under dynamic vacuum conditions at ambient temperature. The adduct "THF.AlEt$_3$" was isolated in a near-quantitative yield (95%) in the form of a colourless liquid. $^1$H NMR analysis confirmed the THF/AlEt$_3$ molar ratio to be 1.03/1.

$^1$H NMR: (300 MHz, CD$_2$Cl$_2$); δ(ppm): 4.12 (m, 4H); 2.11 (m, 4H); 1.04 (t, 9H); −0.18 (q, 6H).

Examples 2-10

The ethylene dimerization tests presented in Table 1 below were carried out in a stainless steel autoclave with a useful volume of 500 mL, provided with a jacket in order to regulate the temperature by oil circulation. Stirring was provided using a Rushton impeller with a mechanical drive. 40 mL of n-heptane as well as 5 mL of a 0.085 mol/L solution of titanium compound in n-heptane were introduced into this reactor under an atmosphere of ethylene and at ambient temperature. Once the temperature of the reactor had reached 53° C., the desired quantity of aluminium-based co-catalyst (already diluted in n-heptane) was introduced under ethylene pressure. For Examples 2 to 4 (comparative), the aluminium-based co-catalyst was AlEt$_3$. For Examples 5 to 10 (in accordance with the invention), the aluminium-based co-catalyst was the adduct THF-AlEt$_3$ synthesised in Example 1. The ethylene pressure was maintained at 23 MPa and the temperature was maintained at 53° C. After a time "t" for reaction (see Table 1), ethylene introduction was halted and the reactor was cooled to 25° C. The reactor was then degassed through a gas meter. This gas was analysed by gas phase chromatography. The liquid phase contained in the reactor was then weighed and analysed by gas phase chromatography. The polymer, if present, was recovered, dried and weighed. The composition of the products obtained is given in Table 1 below.

In Table 1, the activity is defined as the mass of ethylene consumed per gram of titanium initially introduced per hour. The % $C_4$ corresponds to the quantity of olefins containing 4 carbon atoms in the total distribution. The % $C_4^{=1}$ represents the selectivity for 1-butene in the $C_4$ cut. The quantity of polymer (% PE) corresponds to the mass of polymer recovered, as a function of the total distribution.

TABLE 1

| Ex. | Titanium compound "Ti" | Co-catalyst "Al" | Al/Ti ratio | Time (min) | Activity (g/gTi/h) | % $C_4$ (% $C_4^{=1}$) | % PE |
| --- | --- | --- | --- | --- | --- | --- | --- |
| 2 | [Ti(O"Bu)$_4$] | AlEt$_3$ | 3 | 73 | 7400 | 91 (99$^+$) | 0.79 |
| 3 | [Ti(O"Bu)$_4$]/4THF** | AlEt$_3$ | 3 | 87 | 6200 | 94 (99$^+$) | 0.05 |
| 4 | [Ti(O"Bu)$_4$]/4THF** | AlEt$_3$ | 6.8 | 62 | 12400 | 94 (99$^+$) | 0.30 |
| 5 | [Ti(O"Bu)$_4$] | THF—AlEt$_3$ | 2 | 120 | 4100 | 95 (99+) | nd* |
| 6 | [Ti(O"Bu)$_4$] | THF—AlEt$_3$ | 4 | 72 | 7900 | 94 (99+) | nd* |
| 7 | [Ti(O"Bu)$_4$]/4THF** | THF—AlEt$_3$ | 2.5 | 94 | 5700 | 94 (99+) | nd* |
| 8 | [Ti(O"Bu)$_4$]/4THF** | THF—AlEt$_3$ | 3 | 86 | 6300 | 94 (99+) | nd* |
| 9 | [Ti(O"Bu)$_4$]/4THF** | THF—AlEt$_3$ | 4 | 79 | 7500 | 94 (99+) | nd* |
| 10 | [Ti(O"Bu)$_4$]/4THF** | THF—AlEt$_3$ | 6 | 49 | 11000 | 92 (99+) | nd* |

*nd = not detected (this designation characterizes the total absence of polymer).
**The titanium compound is used as a mixture with the THF in a THF/Ti molar ratio of 4.

In this table, Examples 2 to 4 are given by way of comparison (not in accordance with the invention). Examples 5 to 10 show that the use of a preformed adduct between a Lewis base, in this case THF, and the triethylaluminium of the invention means that very good activity and selectivity can be obtained for the selective dimerization of ethylene to 1-butene while minimizing the production of polyethylene to a threshold below the limit of detection.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding French Application No. 14/56471, filed Jul. 4, 2014 are incorporated by reference herein.

The invention claimed is:

1. A catalytic composition comprising at least one alkoxy or aryloxy titanium compound and at least one preformed mixture of a Lewis base (LB) additive and an aluminium compound (Al),
    wherein the aluminium compound (Al) is a tris(hydrocarbyl)aluminium compound of the formula AlR"$_3$ in which R" is a hydrocarbyl radical and wherein the composition is provided as a solution containing the recited components in solution, and
    wherein the Lewis base (LB) additive is a cyclic ether which may be substituted or not substituted with alkyl, aryl, or aralkyl groups containing 2 to 30 carbon atoms,
    wherein a molar ratio LB/Al is greater than 0.5 and less than or equal to 5,
    wherein the at least one alkoxy or aryloxy titanium compound is in mixture with an ether solvent, in a molar ratio between the ether solvent and the at least one alkoxy or aryloxy titanium compound in the range of 20/1 to 1/1, and
    wherein a molar ratio of the aluminium compound and the titanium compound is in the range of 1/1 to 100/1.

2. The catalytic composition according to claim 1, wherein the aluminium compound (Al) is a tris(hydrocarbyl) aluminium compound of the formula AlR"$_3$ in which R" is an alkyl radical containing 1 to 6 carbon atoms.

3. The catalytic composition according to claim 1, which comprises an alkoxy titanium compound of the formula [Ti(OR)$_4$], in which R is a linear or branched alkyl radical containing 2 to 30 carbon atoms.

4. The catalytic composition according to claim 1, which comprises an aryloxy titanium compound of the formula [Ti(OR')$_4$], in which R' is an aryl radical which may or may not be substituted with alkyl, aryl or aralkyl groups containing 2 to 30 carbon atoms.

5. The catalytic composition according to claim 1, in which the preformed mixture of the Lewis base (LB) additive and the aluminium compound (Al) is used as a mixture with a solvent selected from the group consisting of aliphatic and cyclo-aliphatic hydrocarbons, unsaturated hydrocarbons, diolefins, and aromatic hydrocarbons, pure or as a mixture.

6. A process for the preparation of a catalytic composition according to claim 1, which comprises preparing the preformed mixture by adding the Lewis base (LB) additive to the aluminium compound (Al).

7. The process for the preparation of the catalytic composition according to claim 6, in which the preformed mixture is prepared at a temperature in the range −80° C. to +200° C.

8. The process according to claim 6, wherein the preformed mixture is prepared in a medium which is diluted using a solvent.

9. A process for the selective dimerization of ethylene to 1-butene which comprises contacting ethylene with the catalytic composition according to claim 1.

10. The process for the selective dimerization of ethylene to 1-butene according to claim 9, in which the dimerization reaction is carried out at a total pressure of 0.5 to 20 MPa and at a temperature of 20° C. to 180° C.

11. The process for the selective dimerization of ethylene to 1-butene according to claim 9, in which the selective ethylene dimerization reaction is carried out in a batch or continuous mode.

12. The process for the selective dimerization of ethylene to 1-butene according to claim 9, carried out such that solutions of the titanium compound and preformed mixture of the Lewis base additive and the aluminium compound are introduced into a reactor provided with stirring, heating and cooling means, then pressurizing the reactor with ethylene and adjusting the temperature.

13. The process for the selective dimerization of ethylene to 1-butene according to claim 9, wherein the titanium compound and the preformed mixture of the Lewis base additive and the aluminium compound are separately introduced into a reactor maintained under a constant pressure of ethylene.

14. The process for the selective dimerization of ethylene to 1-butene according to claim 9, wherein the titanium compound and the preformed mixture of the Lewis base additive and the aluminium compound are introduced into a first reactor/mixer, and said composition is then continuously introduced into a second reactor maintained under a constant pressure of ethylene.

* * * * *